US00PP31476P2

(12) United States Plant Patent
Olesen et al.

(10) Patent No.: US PP31,476 P2
(45) Date of Patent: Feb. 25, 2020

(54) ***CLEMATIS* PLANT NAMED 'EVIPO083'**

(50) Latin Name: *Clematis viticella*
Varietal Denomination: Evipo083

(71) Applicants: Mogens Nyegaard Olesen, Fredensborg (DK); Raymond J. Evison, St Sampsons Vale (GB)

(72) Inventors: Mogens Nyegaard Olesen, Fredensborg (DK); Raymond J. Evison, St Sampsons Vale (GB)

(73) Assignee: POULSEN ROSER A/S, Fredensborg (DK)

( * ) Notice: Subject to any disclaimer, the term of this patent is extended or adjusted under 35 U.S.C. 154(b) by 0 days.

(21) Appl. No.: 15/999,906

(22) Filed: Sep. 10, 2018

(51) Int. Cl.
*A01H 5/02* (2018.01)
*A01H 6/72* (2018.01)

(52) U.S. Cl.
USPC ..... Plt./228
CPC ..... *A01H 6/72* (2018.05)

(58) Field of Classification Search
USPC ..... Plt./228
CPC ..... A01H 6/72; A01H 5/02
See application file for complete search history.

(56) References Cited

PUBLICATIONS

Poulsen Roser (http://www.poulsenroser.com/assortment/clematis-collections/boulevard/daiyu.aspx; retrived from Google search Jun. 17, 2019).*

* cited by examiner

*Primary Examiner* — Keith O. Robinson

(57) ABSTRACT

A new *Clematis* plant with a compact growth habit, profuse, red-purple flowers, and continuous summer flowering. The variety successfully propagates from softwood cuttings and is suitable for cultivation in commercial nursery culture. This new and distinct variety has shown to be uniform and stable in the resulting generations from asexual propagation from vegetative cuttings.

1 Drawing Sheet

Botanical Classification: Genus: *Clematis*. Species: *viticella*.

Variety Denomination: 'Evipo083'.

SUMMARY OF THE CLAIMED PLANT

The present invention constitutes a new and distinct variety of *Clematis* plant which originated from a controlled crossing between the female seed parent, an un-named seedling, and the male pollen parent, an un-named seedling. Both parent varieties are non-patented.

The two parents were crossed during the summer of 2005 and the resulting seeds were planted the following winter in a controlled environment in Guernsey, Channel Islands, United Kingdom. The new variety named 'Evipo083' originated as a single seedling from the stated cross.

The new *clematis* plant may be distinguished from its female seed parent and male pollen parent by the following characteristics. The female seed parent has red tepals while the new variety has red-purple tepals. The male seed parent has a growth height of 100 cm, while new variety grows to about 55 cm.

The objective of the hybridization of this *clematis* plant was to create a new and distinct variety for nursery culture with unique qualities such as:

1. Uniform and abundant red-purple flowers;
2. Vigorous and compact growth, making the variety suitable for container culture; and
3. Improved disease resistance.

This combination of qualities was lacking in *clematis* plants that were in commercial cultivation and the qualities have been substantially achieved in the new variety.

'Evipo083' was selected by Mogens N. Olesen and Raymond J. Evison in their *clematis* development program in the Channel Islands, United Kingdom in 2006. Asexual reproduction of 'Evipo083' by means of vegetative stem cuttings and traditional layering was first performed by Mogens N. Olesen and Raymond J. Evison in the nursery during the summer of 2006. This initial and subsequent asexual propagations have demonstrated that the characteristics of 'Evipo083' are true to type and are transmitted from one generation to the next.

BRIEF DESCRIPTION OF THE DRAWING

The accompanying color illustration shows as true as is reasonably possible to obtain in color photographs of this type the typical characteristics of the buds, flowers, leaves, and stems, of 'Evipo083'. Specifically illustrated in the drawing are bare stems, a cluster of flowers on the branch, open flower viewed from above, tepals detached, reproductive flower parts, and leaves. Illustrated plants are 2 years of age.

DETAILED DESCRIPTION OF THE VARIETY

The following is a detailed description of 'Evipo083', as observed in its growth throughout the flowering period in Marion County Oreg. Observed plants were cultivated for a period of 24 months in an open field. Certain phenotypical characteristics of the variety may vary under different environmental, cultural, agronomic, seasonal, and climatic conditions. Color references are made using The Royal Horticultural Society (London, England) Colour Chart, 2001, except where common terms of color are used.

For a comparison, several physical characteristics of the *clematis* variety 'Evipo056' described and illustrated in U.S. Plant Pat. No. 27,279 are compared to 'Evipo083' in Chart 1.

CHART 1

| | 'Evipo083' | 'Evipo056' |
|---|---|---|
| Flower diameter | 120 mm | 80 to 100 mm |
| Tepal upper surface after opening | Red-Purple Group 61A with intonations of Red-Purple Group 61C at the central bar zone. | Purple-Violet Group 82C with a central stripe Purple-Violet Group 81A |
| Height of plant | 55 cm | 100 to 150 cm |

Flower and Flower Bud

Blooming habit: Continuous. The natural flowering period is generally from April to September.

Flower bud:

*Size.*—Normally 42 mm in length. Bud diameter is 19 mm.

*Bud form.*—Elliptic.

*Bud color.*—Yellow-Green Group 145B.

*Texture.*—Pubescent.

Pedicel:

*Surface texture.*—Slightly pubescent.

*Length.*—On average 30 mm in length with 2 mm diameter.

*Color.*—Yellow-Green Group 145B.

*Strength.*—Moderately strong.

Receptacle:

*Surface texture.*—Lightly pubescent.

*Shape.*—Broad funnel.

*Size.*—1 mm (h)×2 mm (w).

*Color.*—Yellow-Green Group 145B.

Flower arrangement:

*Location on vine.*—New and old growth, at the terminal and axillary buds along the stem.

*Borne.*—Each stem produces 10 to 20 flowers, borne solitary.

Flower bloom:

*Size.*—On average, flowers are 120 mm in diameter 20 mm in depth.

*Profile.*—Open flowers flat.

*Attitude.*—Upwards.

*Fragrance.*—None.

*Lasting quality.*—Flowers normally remain up to 10 days on the plant.

Tepals:

*Tepal color.*—The upper surface is Red-Purple Group 61A with intonations of Red-Purple Group 61C at the central bar zone. The lower surface is Purple Group N77B with a central bar of Purple Group 76C and innermost color of Yellow-Green Group 145D.

*Quantity.*—Single. Normally 7 tepals.

*Size.*—65 mm long by 40 mm wide.

*Overlap.*—Partial overlapping.

*Shape.*—Individual tepal shape elliptic. The tepal apex is acute. The tepal base is acute.

*Apex recurvature.*—Recurved slightly.

*Tepal cross section.*—Reflexed.

*Margins.*—Entire. Moderate undulations of margin observed.

*Persistence.*—Tepals drop off cleanly.

Reproductive organs:

*Pollen.*—None observed.

*Anthers.*—Size: 6 mm in length. Color: Greyed-Purple Group N186A. Quantity: On average, 55.

*Filaments.*—Color: White Group 155A. Length: 10 mm.

*Pistils.*—Quantity: On average, 20.

*Stigmas.*—Inferior in location relative to the length of the filaments and the height of the anthers.

*Styles.*—Color: Green-White Group 157A. Length: 10 mm.

Seed head characteristics: Seed not observed to date.

Plant

Plant form: Climbing.

Plant growth: Compact.

Size: Seasons growth attains an average of 55 cm in height. Average spread is 60 cm.

Stems:

*Color.*—Juvenile stems are Yellow-Green Group 144B with intonations of Greyed-Red Group 179A. Mature stems are Greyed-Purple Group 184B.

*Internodes.*—On average, 85 mm between nodes.

*Length.*—Normally 20 cm from the base of the plant to the flowering portion of the stem.

*Diameter.*—About 3 mm.

*Texture.*—Mature stems are ribbed.

Plant foliage:

*Leaf characteristics.*—Deciduous.

*Arrangement.*—Ternate.

*Leaf size.*—Compound leaves are about 110 mm (l)× 110 mm (w). Leaflets are about 70 mm (l)×45 mm (w).

*Abundance.*—On average 1 leaf per 10 cm of stem.

*Leaf color.*—Juvenile upper Yellow-Green Group 144A with Greyed-Purple Group 183B at the margins. Juvenile lower Yellow-Green Group 144A. Mature upper Yellow-Green Group 146A. Mature lower Yellow-Green Group 146A.

*Stipules.*—Absent.

*Petioles.*—Size: Normally 30 mm in length by 2 mm diameter. Texture: Smooth. Color: Greyed-Purple Group 183A.

*Petioloule.*—Size: About 10 mm in length by 2 mm diameter.

*Texture.*—Smooth.

*Color.*—Greyed-Purple Group 183A.

*Leaflet shape.*—Cordate, to elliptic. The apex is acute, the base is rounded.

*Margin.*—Entire.

*Surface.*—The upper side is smooth, the lower side is smooth.

*Thickness.*—Average.

*Glossiness.*—Moderately glossy.

Disease resistance: Subject to any disease that normally attacks the species. However the variety is more tolerant to *clematis* wilt, *Ascochyta clematidina*, than some *clematis* known to the inventors.

Cold hardiness: The variety is tolerant to USDA Hardiness Zone 6.

Heat tolerance: The variety has been found to be suitable for climate conditions found in the American Horticulture Society heat zone 7.

We claim:

1. A new and distinct variety of *clematis* plant named 'Evipo083', substantially as described and illustrated , due to its abundant red-purple flowers with good keepability, attractive long lasting foliage and compact growth, year round flowering under glasshouse conditions, suitability for production from softwood cuttings in pots, durable flowers and foliage which make the variety suitable for distribution in the floral industry.

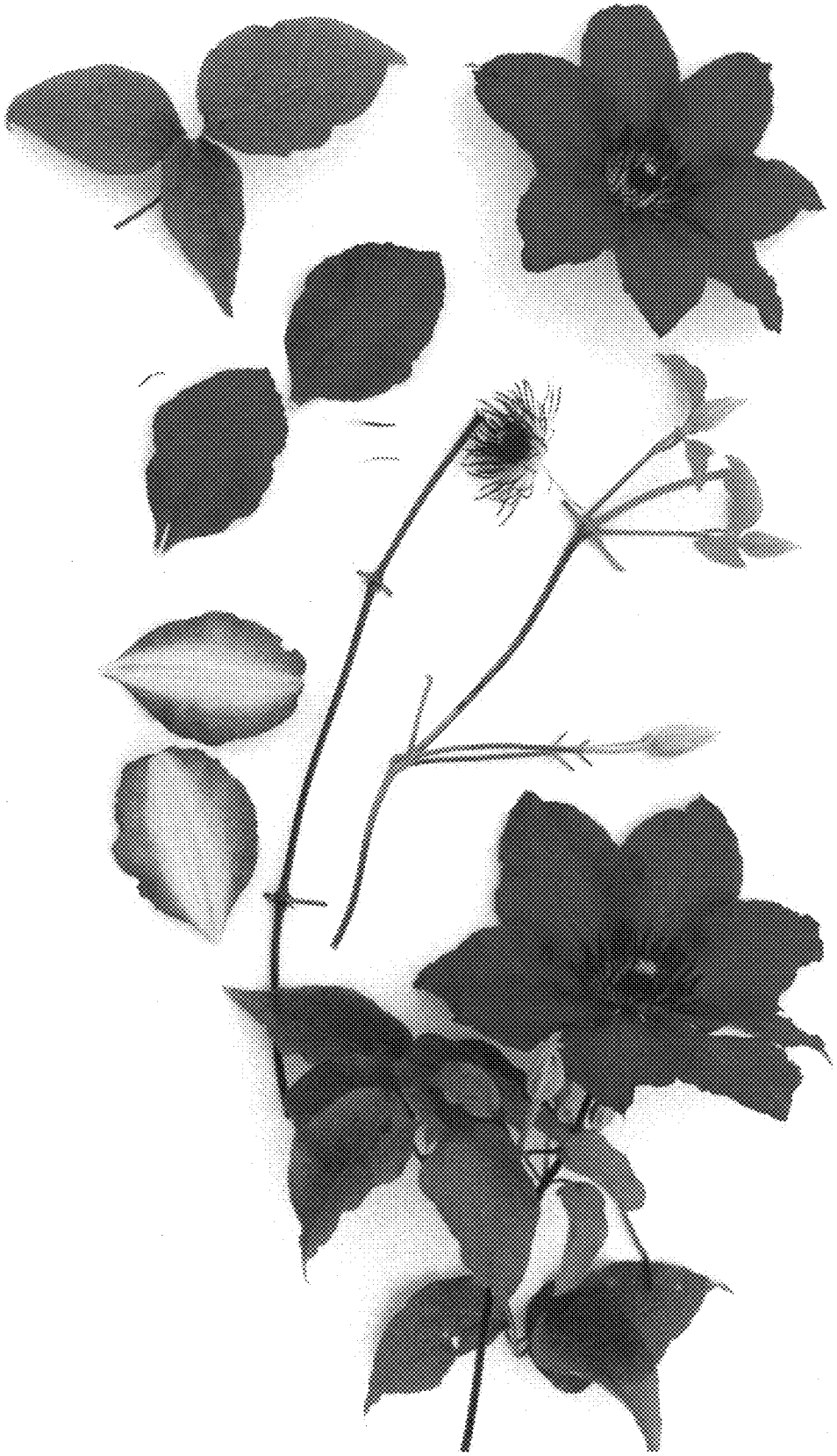

* * * * *